United States Patent [19]

Kariyone et al.

[11] Patent Number: 5,242,793
[45] Date of Patent: Sep. 7, 1993

[54] SELECTIVE PERMEABLE MEMBRANE AND ELECTRODE USING THE SAME

[75] Inventors: Akio Kariyone, Kyoto; Ryuzo Hayashi, Higashiosaka; Yoshio Hashizume, Kakogawa, all of Japan

[73] Assignee: Kanzaki Paper Manufacturing Co., Ltd., Tokyo, Japan

[21] Appl. No.: 490,709

[22] Filed: Mar. 7, 1990

[30] Foreign Application Priority Data

Mar. 8, 1989 [JP] Japan .................. 1-57588
Mar. 27, 1989 [JP] Japan .................. 1-75623

[51] Int. Cl.$^5$ .................. C12N 11/08; C12Q 1/25; C25B 11/04; G01N 27/26
[52] U.S. Cl. .................. 435/4; 204/290 R; 204/291; 204/403; 435/180; 435/817; 530/362
[58] Field of Search .................. 204/403, 284, 290 R, 204/291, 292; 435/4, 817, 180, 182; 530/362

[56] References Cited

U.S. PATENT DOCUMENTS

| | | | |
|---|---|---|---|
| 4,224,125 | 9/1980 | Nakamura et al. | 435/4 |
| 4,659,665 | 4/1987 | Freeman et al. | 435/182 |
| 5,034,330 | 7/1991 | Yamori et al. | 435/180 |

FOREIGN PATENT DOCUMENTS

| | | |
|---|---|---|
| 0276782A2 | 3/1988 | European Pat. Off. . |
| 55-164349 | 12/1980 | Japan . |
| 58-49821 | 11/1983 | Japan . |
| 60-56254 | 4/1985 | Japan . |
| 61-245051 | 10/1986 | Japan . |
| 62-32352 | 2/1987 | Japan . |
| 63-78062 | 4/1988 | Japan . |
| 63-182559 | 7/1988 | Japan . |

OTHER PUBLICATIONS

Toyobo Co. Ltd., Chem. Abs. vol. 94 No. 25 Entry #205036 d (1981).
Katayama, Chem. Abs. vol. 110 No. 25 Entry #228160c (1989).

*Primary Examiner*—Jeffrey E. Russel
*Attorney, Agent, or Firm*—Wenderoth, Lind & Ponack

[57] ABSTRACT

An electrode comprising an electrically conductive base, and a selectively permeable membrane which is produced by forming a membrane from a mixed solution comprising (a) albumin, (b) at least one type of crosslinking agent and (c) chitosan. The selectively permeable membrane is useful, e.g., in conjuction with an electrode. An enzyme electrode is also provided having the selectively permeable membrane disposed on the electrode and an immobilized enzyme membrane disposed on the selectively permeable membrane. The immobilized enzyme membrane is prepared by incorporating a carboxylate into the solution containing the enzyme and an aldehyde as the crosslinking agent. The crosslinking is effected by heating or drying.

9 Claims, 1 Drawing Sheet

Fig. 1

SELECTIVE PERMEABLE MEMBRANE AND ELECTRODE USING THE SAME

BACKGROUND OF THE INVENTION

1. Field of the Invention

The present invention relates to a selective permeable membrane and an electrode using it to be favorably employed, for example, in an immobilized biocatalytic electrode in a system for detecting the formation or consumption of a substance which is detectable electrochemically.

2. Description of the Prior Art

The prior art relating to the selective permeable membrane is described below together with the background technology of its application field.

Recently, thanks to the advancement in biochemistry and other studies, the hitherto unknown bioreactions are gradually disclosed to be applied in the fields of chemical industries.

The scope of the biochemical reactions catalyzed by cells and enzymes is broad, and in particular attention is focused on the so-called biosensing field which is intended to apply the biochemical reaction as the means for detection of substances. By the use of biosensing techniques, the hitherto immeasurable substances or substances which took too much time and labor to measure can now be measured easily, and it is being practically employed in the fields of environmental measurement, food analysis, and medical analysis.

Generally, the biocatalysts such as enzymes involve many advantages including:

1. High specificity of reaction.
2. Capability of measurement in mild conditions.
3. High sensitivity to measure trace substances.

By contrast, since biological materials are used as the catalysts, the following disadvantages are also known.

1. Biocatalysts such as enzymes are expensive.
2. Reaction conditions such as temperature and pH are limited.
3. The catalytic function of biocatalysts such as enzymes is lost by various factors, that is, inactivation occurs.

To solve such problems, it is proposed to immobilize the biocatalysts, and many methods have been presented so far. Among them, the method of immobilizing the biocatalyst by using a covalent bonding crosslinking agent by crosslinking reaction is preferred for practical use because its bond is firm as compared with adsorption or ion bonding.

When applying such immobilized biocatalyst in measurement of a substance, a biocatalyst is used in combination with the detection means for detecting a substance formation or consumption depending on its biochemical reaction. As such detection means, an electrochemical detector, a fluorescent detector, a thermal detector, or the like may be applied. In particular, the electrochemical detecting method of consumption of oxygen or formation of hydrogen peroxide in biochemical reaction by an immobilized enzyme is most widely employed because of the simplicity of apparatus compositon, high sensitivity of detection, and speed of reaction rate.

However, when the hydrogen peroxide electrode is used, not only the hydrogen peroxide produced by biochemical reaction, but also undesired substances such as ascorbic acid contained in the sample are detected, and the reliability of measurement is known to be lowered. To solve this problem, it is attempted to place a selective permeable membrane between the immobilized enzyme membrane and the hydrogen peroxide electrode. That is, near the surface of the hydrogen peroxide electrode, a selective permeable membrane for limiting permeation of substances other than the object substance and an immobilized enzyme membrane are disposed in this order through a buffer solution or the like, or a selective permeable membrane and an immobilized enzyme membrane are directly formed in this order on the electrode surface. As a result, detection of undesired substances may be prevented, while the precision of measurement may be enhanced.

Conventionally as such a selective permeable membrane, for example, acetyl cellulose was used as disclosed in the Japanese Laid-open Patent No. 60-56254. To manufacture such selective permeable membrane, however, it is necessary to use an organic solvent that is hard to handle. Moreover, in order to obtain a desired selective permeability, the drying time and other conditions must be adjusted delicately, which requires an enormous amount of time and a complicated operation.

The present inventors have previously proposed a method of forming a selective permeable membrane easily by using protein and crosslinking agent (the Japanese Laid-open Patent No. 63-182559). However, not limited to selective permeable membranes, generally, the immobilized protein membranes formed by using protein and crosslinking agent are low in physical strength, and are hard to handle, and the durability is inferior.

The problem of such physical strength of immobilized protein membrane cannot be radically solved even if the protein is immobilized on a carrier having a high physical strength, for example, because the immobilized protein membrane itself is brittle and may be partly exfoliated.

Thus, the problems of the selective permeable membrane still remain unsolved at the present without proposal of any effective solutions. Generally, while not directed to a selective permeable membrane, the method of enhancing the strength of immobilized protein membrane formed by immobilizing the protein which is a biocatalyst such as enzyme is disclosed, for example, in the Japanese Patent Publication No. 58-49821. In this method, the enzyme as biocatalyst is immobilized together with amino and imino high polymers, and the physical strength of the enzyme immobilized membrane is enhanced. When this method is applied in the selective permeable membrane, however, the properties of immobilized protein may be changed, and it is difficult to obtain a desired selective permeability.

Futhermore, as disclosed in the Japanse Laid-open Patent No. 62-32352, a method of reinforcing the strength of enzyme immobilized membrane by immobilizing the enzyme which is a protein on a polyester cloth is proposed. In this method, however, the thickness of the protein membrane increases, and when applied in formation of selective permeable membrane, the measuring sensitivity and speed of the immobilized enzyme electrode are worsened.

Hereinbelow is a description of the prior art relating to immobilized enzyme membrane together with the background technology of its application field.

The methods for immobilizing enzyme may be roughly classified as follows:

1. The absorbing method to immobilize the enzyme by physically absorbing it on a water-insoluble carrier.

2. The crosslinking method to make the enzyme insoluble by a crosslinking reaction between the enzyme and another enzyme or protein by using a reagent having multi functional groups.

3. The entrapping method to wrap the enzyme in a fine lattice of high molecular gel or to cover it with a capsule of semipermeable high molecular membrane.

Among these methods, the crosslinking method is relatively widely used because the enzyme is firmly immobilized and the operation for immobilizing the enzyme is relatively easy. In particular, aldehydes as represented by glutaraldehyde are high in reactivity with enzyme, and the enzyme can be immobilized in a relatively moderate conditions, and hence they are used widely.

In the immobilizing method of an enzyme using aldehydes, for example, a mixed solution of the enzyme to be immobilized and aldehyde is prepared in advance. Next, this mixed solution is applied on the carrier or this carrier is dipped in the mixed solution (immersion method), and an immobilized enzyme membrane is formed. In the immersion method, however, it is difficult to control accurately the amount of the solution on the carrier surface, and hence it is difficult to control the immobilizing amount of enzyme precisely.

On the other hand, when a specific volume of mixed solution is applied on the carrier in order to immobilize the enzyme with high reproducibility, the enzyme and its crosslinking reagent of aldehyde are mixed preliminarily, and the crosslinking reaction is gradually progressed in the mixed solution. Therefore, in the case of continuous mass production of a multiplicity of immobilized enzyme, the mixed solution may be immobilized in the midst of production process. For example, as proposed in the Japanese Laid-open Patent No. 61-245051, in the case of formation of a quantity of immobilized protein membranes by continuously ejecting a mixed solution of protein and aldehyde from the nozzle, the viscosity of the mixed solution of protein and aldehyde is gradually raised to be finally immobilized, and therefore it is difficult to form the immobilized protein membranes continuously in some degree.

Therefore, in order to immobilize the enzyme homogeneously with high reproducibility, it is desired to prepare preliminarily a mixed solution of enzyme and aldehyde at specific ratio, apply it on the carrier, and start crosslinking reaction. In this method, the excellent enzyme electrode is obtained, however, there is the problem of lowering of the working efficiency due to increase of viscosity and hardening of the mixed solution in the manufacturing process.

SUMMARY OF THE INVENTION

It is hence a primary object of the invention to provide a selective permeable membrane and an electrode using the same, possessing a desired selective permeability, excellent in physical strength, and easy to manufacture, by solving the technical problems discussed above.

To achieve this object, the invention provides a selective permeable membrane produced by extending a mixed solution comprising a protein, at least one type of crosslinking agent, and at least one type of high molecular substance reacting with the crosslinking agent, aside from the protein, in a membrane form, and immobilizing the protein by a crosslinking reaction.

According to a preferred embodiment, the protein contains at least one type of globular protein, and the crosslinking agent contains a crosslinking agent, for crosslinking with an amino group, and the high molecular substance contains a linear polysaccharide possessing either amino group or derivative of amino group, or both.

In other preferred embodiment, the composition ratio by weight of the protein and the linear polysaccharide is in a range of 1000:1 to 1000:10, while the composition ratio by weight of the protein and the crosslinking agent is preferably in a range of 100:5 to 100:50.

In another preferred embodiment, the protein is at least one selected from albumin, globulin and prolamin, the crosslinking agent is glutaraldehyde and/or hexamethylene di-isocyanate, and the linear polysaccharide is chitosan.

The invention also presents an electrode having the selective permeable membrane disposed on the surface or in the vicinity of an electrically conductive base.

In such electrode, an immobilized enzyme membrane having at least one enzyme, preferably oxidase, may be disposed on the surface or in the vicinity of the selective permeable membrane, the opposite side to the electrically conductive base.

It is the second object of the invention relating to a enzyme immobilized membrane to present an immobilizing method of enzyme, capable of preventing undesired crosslinking and hardening in the midst of manufacturing process when immobilizing enzyme by using aldehydes, and immobilizing enzyme continuously, quantitatively and at high reproducibility without impeding the crosslinking and hardening process, and also an enzyme immobilized membrane formed by this method.

To achieve the above object, the preferred embodiment of the invention presents an immobilizing method of enzyme by crosslinking with an aldehyde used as a crosslinking agent, comprising the steps of:

containing coexistently at least one type of carboxylate in a mixed solution of enzyme and aldehyde, and heating or drying to promote the crosslinking reaction, thereby immobilizing the enzyme.

The immobilized enzyme membrane formed in this manner may be preferably embodied as an immobilized enzyme membrane of enzyme electrode in relation to the selective permeable membrane described above.

As stated above in relation to the description of the prior art, when protein is immobilized on or near the surface of an electrically conductive base and used as a selective permeable membrane, and an immobilized enzyme membrane is further formed to compose an immobilized enzyme electrode, the physical strength of the selective permeable membrane largely influences the life time of the immobilized enzyme electrode.

The selective permeable membrane according to the invention is described hereinafter.

Generally, to enhance the physical strength of an immobilized protein membrane, it is enough to raise the concentration of the crosslinking agent in the immobilized protein membrane. However in the case of forming the immobilized protein membrane as selective permeable membrane, the physical properties of the immobilized protein membrane change because of high concentration of the crosslinking agent, and the selective permeability may be lowered, which is not preferable.

It is also known to enhance the strength of the immobilized protein membrane by coexistence of a reinforcing substance to react with the crosslinking agent in the immobilized protein membrane. In such conventional method, however, the reinforcing substance adversely affects the physical properties of the immobilized protein membrane, and the intrinsic function as the selective permeable membrane, that is, the selectivity, may be sacrificed.

Accordingly, the present inventors attempted an experiment on coexistence of reinforcing substance to react with the crosslinking agent in the selective permeable membrane composed of protein and crosslinking agent, in particular, and conduct investigations in search for a reinforcing substance capable of enhancing the physical strength of the selective permeable membrane without adversely affecting the physical properties of the selective permeable membrane, and its manufacturing condition, and finally reached this invention.

The required properties for such reinforcing substance may include the following:

1. The substance should be dissolved in the solution of the protein to be immobilized, or in a mixed solution of this protein and crosslinking agent.
2. A small quantity of the substance should be capable of enhancing the physical strength of the selective permeable membrane so as not to adversely affect the physical properties of the selective permeable membrane.
3. The substance should be reactive to the crosslinking agent, at the same level as the protein to be immobilized, and should be made insoluble by the crosslinking reaction.

Therefore the present inventors searched for a substance that can coexist in a mixed solution of protein and crosslinking agent, react with the crosslinking agent, and be free from adverse effects on the selective permeability of the selective permeable membrane.

For example, using glutaraldehyde as the crosslinking agent and distilled water or buffer solution as the solvent, a mixed solution of protein and crosslinking agent at specific concentration was prepared, and various substances were put in this mixed solution to perform a crosslinking reaction with glutaraldehyde, and immobilized protein membranes were fabricated. By testing the physical strength and selective permeability of thus obtained immobilized protein membranes, the substances capable of enhancing the physical strength of the selective permeable membrane without adversely affecting the selective permeability may be found.

As a result it was discovered that the physical strength of the immobilized protein membrane can be enhanced without adversely affecting the selective permeability of the immobilized protein membrane, by using a protein comprising at least one type of globular protein, by using a compound capable of crosslinking with an amino group as the crosslinking agent, and by using a linear polysaccharide comprising an amino group, derivative of an amino group, or both, as the compound to coexist in the mixed solution.

According to the invention, an excellent selective permeable membrane can be formed easily. In particular, it is easily possible to dispose the selective permeable membrane directly on the surface of an electrically conductive base, and moreover an immobilized enzyme electrode is manufactured by forming an immobilized enzyme membrane on the selective permeable membrane according to the method described below.

Various crosslinking agents is used in the invention, and in particular glutaraldehyde, hexamethylene diisocyanate and other crosslinking reagents are high in the bonding strength and are used preferably. Above all, glutaraldehyde is desirable.

The composition ratio by weight of protein and crosslinking agent is preferably in a range of 100:5 to 100:50 from the viewpoint of the selective permeability of the obtained selective permeable membrane.

The protein used in the selective permeable membrane of the invention contains at least one type of globular protein such as albumin, globulin and prolamin.

The high molecular substance to react with the crosslinking agent being added to the mixed solution of protein and crosslinking agent is a linear polysaccharide comprising an amino group, amino group derivative or both, for example, polysaccharides composed of such composition units of amino sugars such as glucosamine and galactosamine and their derivatives. Such examples may include peptidoglycan of bacteria, partially deacetylated hyaluronic acid, partially deacetylated chondroitin sulfate, and chitosan. The easily available chitosan is preferably used as such high molecular substance.

In the selective permeable membrane of the invention, the composition ratio by weight of protein and linear polysaccharide is preferably in a range of 1000:1 to 1000:10. If the composition ratio by weight of the linear polysaccharide to protein exceeds 1000:10, the selectivity of the selective permeable membrane is lowered to some degree. The cause of worsening the selectivity is unknown, but in case the composition ratio by weight of the linear polysaccharide to protein becomes larger, the concentration of the crosslinking agent to protein lowering relatively, and the crosslinking reaction to protein becomes insufficient. Therefore, the immobilized protein membrane becomes brittle, and adverse effects are brought about to the bonding with the surface of the electrically conductive base, adhesion, and bonding between proteins, and the density of the membrane is not maintained. If the composition ratio by weight is less than 1000:1, the improvement of the membrane strength may not be enough.

According to the invention, to manufacture the selective permeable membrane, first protein and crosslinking agent are dissolved in distilled water or buffer solution, and the high molecular substance is added, and the solution is applied on, for example, the surface of an electrically conductive base. As a result, in the mixed solution containing high molecular substance, the crosslinking reaction is promoted, and an immobilized protein membrane is formed. The thus fabricated selective permeable membrane is very excellent in durability against physical impact such as the shock of ultrasonic treatment. Besides, by the addition of high molecular substance, worsening of selective permeability is avoided.

By disposing the selective permeable membrane of the invention on or above an electrically conductive base, an electrode for measurement of hydrogen peroxide is composed. It is also possible to dispose the selective permeable membrane near the electrically conductive base by way of a buffer solution or the like, but it is otherwise possible to form the selective permeable membrane directly on the electrically conductive base. By immobilizing at least one type of enzyme, preferably oxidase, on the opposite side of the selective permeable membrane to the electrically conductive base, an immobilized enzyme electrode is manufactured. Such immobilized enzyme electrode is high in the physical strength, and is excellent in durability and selectivity of the substance to be detected.

Meanwhile, the selective permeable membrane of the invention may be also used for selectively separating the reaction product, or selectively separating only the raw materials, in the bioreactor.

Preferred embodiments of the immobilized enzyme membrane of the present invention are described hereinafter.

As mentioned in the description of the prior art, when immobilizing enzyme by inducing crosslinking reaction by using a crosslinking agent, in order to control the composition ratio of enzyme and crosslinking agent and perform the crosslinking reaction homogeneously, it is desired to prepare and use a mixed solution with specific composition ratio of enzyme and crosslinking agent. Besides, to immobilize enzyme quantitatively on the surface of the carrier or the like, it is required to apply a specific quantity of the mixed solution.

However, when aldehydes are used as the crosslinking agent, the crosslinking reaction is initiated from the moment of preparation of mixed solution of enzyme and crosslinking agent.

The present inventors, in a method of preliminarily preparing a mixed solution of enzyme and aldehyde and immobilizing the enzyme on the surface of the carrier, investigated for a method of preventing undesired solidification of the mixed solution when applying a specified quantity of mixed solution on the surface of the carrier in order to immobilize the enzyme quantitatively, and finally completed the present invention.

It was found that it is enough to contain at least one type of carboxylates in the mixed solution of enzyme and aldehyde. That is, carboxylates do not form sediments with enzyme, aldehyde or components in buffer solution, and it is also found that the crosslinking reaction is prevented until the time of drying or heating treatment of the mixed solution comprising the carboxylate.

As the type of carboxylic acid in carboxylate, compound of which molecular weight is 300 or less is desired. If the molecular weight exceeds this range, the solubility of the carboxylate becomes small, and it may not be dissolved completely when added to the mixed solution of enzyme and aldehyde, or if dissolved, the crosslinking inhibiting effect is small.

Carboxylate that can coexist in the mixed solution of enzyme and aldehyde using water or buffer solution as solvent may include salts of acrylic acid, ascorbic acid, isovalerianic acid, isobutyric acid, formic acid, valerianic acid, citric acid, glyoxylic acid, hydroxyacetic acid, 2,3-dihydroxypropionic acid, 1,3-propanedicarboxylic acid, succinic acid, acetic acid, oxalic acid, tartaric acid, thioacetic acid, lactic acid, vinyl acetate, pyruvic acid, propionic acid, maleic acid, malonic acid, mandelic acid, acetic anhydride, phthalic anhydride, mesooxalic acid, butyric acid, malic acid, oleic acid and benzoic acid. Or plural types of these carboxylates may be combined. As the types of salts, from the viewpoint of solubility and small effects to the structure of enzyme, sodium salt, potassium salt and magnesium salt are preferable.

The pH of the mixed solution of enzyme and aldehyde containing such carboxylates is preferably in a range of 5 to 8. Generally in the extreme acidic or alkalinic condition, the enzyme can hardly maintain its intrinsic higher degree structure, and the crosslinking of aldehydes is lowered, and hence it is desired to define the pH in the range shown above.

If the concentration of these carboxylates is too low, the desired effect may not be obtained, or if the concentration is too high, the enzyme may be degenerated, and hence a desired range is from 10 mM to 200 mM.

As the aldehyde for crosslinking agent, formaldehyde, glutaraldehyde, succinylaldehyde, dialdehyde starch and others may be used, and among them glutaraldehyde is most preferably used from the viewpoint of avoiding adverse effects, such as degeneration of protein and lowering of activity of enzyme.

By the coexistence of such carboxylate in a mixed solution of enzyme and aldehyde, promotion of crosslinking reaction of enzyme and aldehyde in the mixed solution is impeded, and the mixed solution of enzyme and aldehyde is crosslinked by drying or heating.

The carboxylic acid is sometimes used as the constituent component of buffer solution, and seeing from the fact that the strong buffering ability is in a range of pH 4 or less, its pKa is almost 4.0 or less. Therefore, in the desired pH range of the invention, the carboxylic acid is nearly in dissociated state. On the other hand, the amino group existing on the surface of enzyme and reacting with aldehyde seems to be protonated. When such compound coexists in the water, ion interaction occurs between the amino group on the protein molecule surface and carboxylic acid, which seems to act to impede reaction of aldehyde with amino group. However, when the moisture is evaporated, the carboxylic acid is bonded with the original paired ions, such as sodium ions, and crystallized and removed from the system. Thereafter, the amino group on the enzyme surface and aldehyde react to induce crosslinking and hardening. Besides, the effect is different depending on the molecular weight of the carboxylic acid, which is considered because it becomes more difficult to approach the surface of the enzyme as the molecular weight increases, so that interaction is more likely to occur in the aldehyde with relatively lower molecular weight, such as glutaraldehyde. It is estimated that the intensity of this interaction is stronger in the carboxylic acid at the lower molecular side, at the boundary of about 300 of molecular weight, and in the aldehyde at the higher molecular side.

According to the invention, the enzyme may be efficiently immobilized on the carrier for immobilized biocatalyst used widely. In particular, where it is required to immobilize enzyme in a membrane form, such as in the immobilized enzyme electrode, the working efficiency may be enhanced, and continuous mass production is realized.

BRIEF DESCRIPTION OF THE DRAWINGS

The objects of the invention, as well as the features and advantages thereof, will be better understood and appreciated from the following detailed description taken in conjunction with the drawings, in which.

DETAILED DESCRIPTION OF THE PREFERRED EMBODIMENTS

The preferred embodiments are presented below to describe the invention more specifically, but it must be noted that the invention is not limited to these embodiments alone. In the following explanation, % refers to wt. %.

Measuring apparatus

Figure 1:
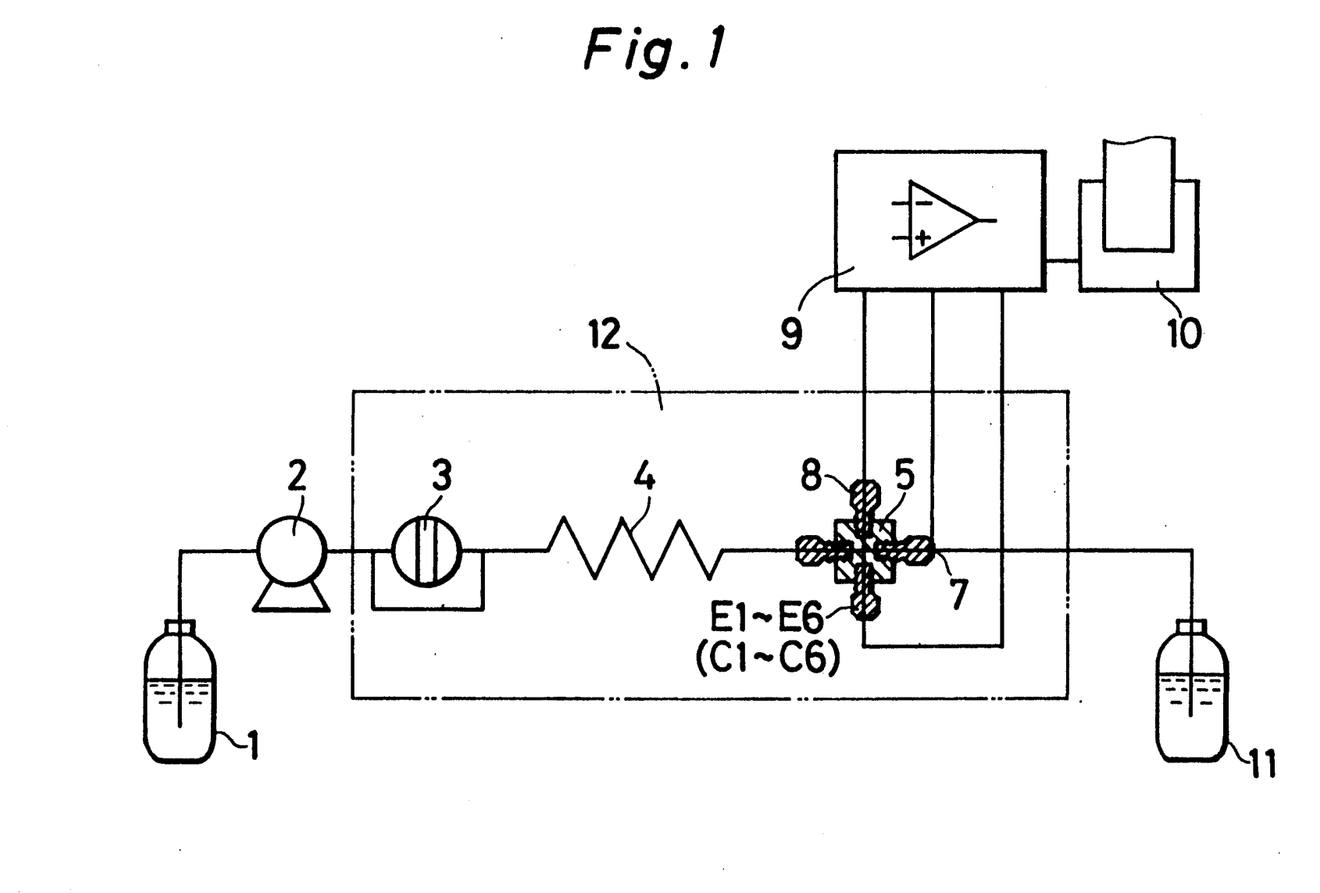
FIG. 1 is a schematic drawing of a flow type measuring apparatus used in an embodiment of the invention and in a reference example.

In the example, a flow type measuring apparatus as shown in FIG. 1 was used. The flow type measuring apparatus shown in FIG. 1 comprises an injector 3 for high speed liquid chromatography capable of injecting sample in the order of μl amount, and a measuring cell 5 containing electrodes E1 to E6 having the selective permeable membrane according to the invention (electrodes C1 to C6 used for comparison), an Ag/AgCl electrode 8 as reference electrode, and a stainless steel duct as a counter electrode 7. For example, a Teflon-made dilution duct 4 of 0.5 mm in inside diameter and 1.5 m in length is connected between the injector 3 and the measuring cell 5. The internal volume of the measuring cell 5 is 40 μl, in which electrodes E1 to E6 (C1 to C6) and Ag/AgCl electrode 8 are disposed opposedly by way of the duct of buffer solution. A voltage of +0.60 V is applied to the electrodes E1 to E6 (C1 to C6) with respect to the Ag/AgCl electrode 8 through a potentiostat 9.

Such structure is placed in a thermostatic oven 12, and the temperature in the thermostatic oven 12 is kept at 37° C. To feed the buffer solution 1, a pump 2 for high speed liquid chromatography is used, and the buffer solution is sent out at a rate of 1.0 ml/min. The buffer solution including the sample after measurement is captured in a waste liquid bottle 11. The measured value is recorded by a recorder 10.

EXAMPLE 1

In order to form the selective permeable membrane of the invention, bovine serum albumin (fraction V, made by Sigma Co.) was used as the protein, glutaraldehyde as the crosslinking agent, and chitosan (made by Tokyo Kasei Kogyo Co.) as the substance reacting with the crosslinking agent other than protein.

Chitosan was dissolved in an aqueous solution of 100 mM of hydrochloric acid, and 0.5% chitosan solution was prepared.

In a Wassermann test tube,

| | |
|---|---|
| 5% bovine serum albumin aqueous solution | 400 μl |
| 25% glutaraldehyde aqueous solution | 20 μl |
| 0.5% chitosan solution | 20 μl |
| distilled water | 560 μl | were mixed, and a mixed solution with the final concentrations of
2% bovine serum albumin
0.5% glutaraldehyde
0.01% chitosan
was prepared.

The composition ratio by weight of protein and chitosan of this mixed solution was 1000:5, and the composition ratio by weight of protein and crosslinking agent was 100:25.

On the other hand, the side surface of a platinum wire of 2 mm in diameter which is an electrically conductive base was coated with a heat-shrink Teflon, and the top of the platinum wire was polished with an emery paper of 1600 count. On the polished surface, 5 μl of the mixed solution was put by using a microsyringe, and dried at 40° C., and a protein membrane was thus directly formed on the platinum electrode. This finished the fabrication of the electrode E1 for detecting hydrogen peroxide.

The electrode E1 made of the platinum electrode thus covered with protein membrane was incorporated into the flow type measuring apparatus shown in FIG. 1, and while passing 100 mM phosphate buffer solution 1 at pH 6.0, a potential of 0.6 V to the Ag/AgCl electrode 8 was applied. In this state, when 5 mM hydrogen peroxide was injected from the injector 3, the detected current was 218 nA. When a solution of 5 mM ascorbic acid was injected, the detected current was 2.9 nA. Therefore, as shown in Table 1, the rate of the detected current due to ascorbic acid to the detected current due to hydrogen peroxide at the same concentration was 1.3%.

TABLE 1

| | Hydrogen peroxide | Ascorbic acid |
|---|---|---|
| Example 1 | 100% | 1.3% |
| Example 2 | 100% | 1.3% |
| Example 3 | 100% | 3.1% |
| Reference 1 | 100% | 62.9% |
| Reference 2 | 100% | 48.5% |
| Reference 3 | 100% | 24.4% |
| Reference 4 | 100% | 1.2% |

Thus fabricated electrode E1 was treated for 10 minutes in an ultrasonic processing apparatus, and then put back into the flow type measuring apparatus shown in FIG. 1. When 5 mM hydrogen peroxide was injected, the detected current was 218 nA, and when a solution of 5 mM ascorbic acid was injected, the detected current was 2.9 nA.

This result is shown in Table 2, together with the result before ultrasonic treatment. It is known from Table 2 that there was no change in the sensitivity of the electrode E1 to hydrogen peroxide and ascorbic acid before and after ultrasonic treatment.

TABLE 2

| | | Detected current before ultrasonic treatment (nA/mM) | Detected current after ultrasonic treatment (nA/mM) |
|---|---|---|---|
| Example 1 | Hydrogen peroxide | 218 | 218 |
| | Ascorbic acid | 2.9 | 2.9 |
| Reference 4 | Hydrogen peroxide | 219 | 262 |
| | Ascorbic acid | 2.6 | 6.6 |

EXAMPLE 2

Bovine serum albumin (fraction V, made by Sigma Co.) was used as the protein, glutaraldehyde as the crosslinking agent, and chitosan (made by Tokyo Kasei Kogyo Co.) as the substance reacting with the crosslinking agent other than protein.

Chitosan was dissolved in an aqueous solution of 100 mM acetic acid, and 0.5% chitosan solution was prepared.

In a Wassermann test tube,

| | |
|---|---|
| 5% bovine serum albumin aqueous solution | 400 μl |
| 25% glutaraldehyde aqueous solution | 20 μl |
| 0.5% chitosan solution | 20 μl |
| distilled water | 560 μl | were mixed, and a mixed solution with the final concentrations of
2% bovine serum albumin
0.5% glutaraldehyde 0.01% chitosan
was prepared.

The composition ratio by weight of protein and chitosan of this mixed solution was 1000:5, and the composition ratio by weight of protein and crosslinking agent was 100:25.

On the other hand, the side surface of a platinum wire of 2 mm in diameter which is an electrically conductive base was coated with a heat-shrink Teflon, and the top of the platinum wire was polished with an emery paper of 1600 count. On the polished surface, 5 µl of the mixed solution was put by using a microsyringe, and dried at 40° C., and a protein membrane was thus directly formed on the platinum electrode. This finished the fabrication of the electrode E2 for detecting hydrogen peroxide.

The electrode E2 made of the platinum electrode thus covered with protein membrane was incorporated into the flow type measuring apparatus shown in FIG. 1, and while passing 100 mM phosphate buffer solution 1 at pH 6.0, a potential of 0.6 V to the Ag/AgCl electrode 8 was applied. In this state, when 5 mM hydrogen peroxide was injected from the injector 3, the detected current was 220 nA. When a solution of 5 mM ascorbic acid was injected, the detected current was 2.9 nA. Therefore, as shown in Table 1, the rate of the detected current due to ascorbic acid to the detected current due to hydrogen peroxide at the same concentration was 1.3%, same as in Example 1. Besides, when the electrode E2 was ultrasonically treated, there was no change in the sensitivity to hydrogen peroxide and ascorbic acid. Therefore, the aqueous solution for dissolving chitosan either hydrochloric acid or acetic acid as far as it is an acidic solution.

EXAMPLE 3

Bovine serum albumin (fraction V, made by Sigma Co.) was used as the protein, glutaraldehyde as the crosslinking agent, and chitosan (made by Tokyo Kasei Kogyo Co.) as the substance reacting with the crosslinking agent other than protein.

Chitosan was dissolved in an aqueous solution of 100 mM hydrochloric acid, and 0.5% chitosan solution was prepared.

In a Wassermann test tube,

| | |
|---|---|
| 5% bovine serum albumin aqueous solution | 400 µl |
| 25% glutaraldehyde aqueous solution | 20 µl |
| 0.5% chitosan solution | 200 µl |
| distilled water | 380 µl | were mixed, and a mixed solution with the final concentrations of

2% bovine serum albumin
0.5% glutaraldehyde
0.05% chitosan
was prepared.

The composition ratio by weight of protein and chitosan of this mixed solution was 1000:25, and the composition ratio by weight of protein and crosslinking agent was 100:25.

On the other hand, the side surface of a platinum wire of 2 mm in diameter which is an electrically conductive base was coated with a heat-shrink Teflon, and the top of the platinum wire was polished with an emery paper of 1600 count. On the polished surface, 5 µl of the mixed solution was put by using a microsyringe, and dried at 40° C., and a protein membrane was thus directly formed on the platinum electrode. This finished the fabrication of the electrode E3 for detecting hydrogen peroxide.

The electrode E3 made of the platinum electrode thus covered with protein membrane was incorporated into the flow type measuring apparatus shown in FIG. 1, and while passing 100 mM phosphate buffer solution 1 at pH 6.0, a potential of 0.6 V to the Ag/AgCl electrode 8 was applied. In this state, when 5 mM hydrogen peroxide was injected from the injector 3, the detected current was 219 nA. When a solution of 5 mM ascorbic acid was injected, the detected current was 6.8 nA. Therefore, as shown in Table 1, the rate of the detected current due to ascorbic acid to the detected current due to hydrogen peroxide at the same concentration was 3.1%. As compared with Examples 1, 2, the selective permeability was slightly inferior, but it was sufficiently practicable. when the electrode E3 was ultrasonically treated, there was no change in the sensitivity to hydrogen peroxide and ascorbic acid.

Reference 1

The side surface of a platinum wire of 2 mm in diameter was coated with a heat-shrink Teflon, and the top surface of the platinum wire was polished with an emery paper of 1600 count to prepare a platinum electrode C1.

This platinum electrode C1 was incorporated into the flow type measuring apparatus, and while passing 100 mM phosphate buffer solution 1 at pH 6.0, a potential of 0.6 V to the Ag/AgCl electrode 8 was applied, and 5 mM hydrogen peroxide was injected, and the detected current was 530 nA, and when 5 mM ascorbic acid solution was injected, the detected current was 333 nA. Therefore, as shown in Table 1, the rate of the detected current due to ascorbic acid to the detected current due to hydrogen peroxide at the same concentration was 62.9%. It is thus found that the sample containing ascorbic acid is subject to the great influence of the ascorbic acid in the platinum electrode C1 without selective permeable membrane.

Reference 2

Bovine serum albumin (fraction V, made by Sigma Co.) was used as the protein, glutaraldehyde as the crosslinking agent, and 1,4-diaminobutane as the substance reacting with the crosslinking agent other than the protein.

In a Wassermann test tube,

| | |
|---|---|
| 5% bovine serum albumin aqueous solution | 400 µl |
| 25% glutaraldehyde aqueous solution | 20 µl |
| 0.5% 1,4-diaminobutane solution | 20 µl |
| distilled water | 560 µl | were mixed, and a mixed solution with the final concentrations of

2% bovine serum albumin
0.5% glutaraldehyde
0.01% 1,4-diaminobutane
was prepared.

On the other hand, the side surface of a platinum wire of 2 mm in diameter which is an electrically conductive base was coated with a heat-shrink Teflon, and the top of the platinum wire was polished with an emery paper of 1600 count. On the polished surface, 5 µl of the mixed solution was put by using a microsyringe, and dried at 40° C., and a protein membrane was thus directly formed on the platinum electrode. This finished the fabrication of the electrode C2 for detecting hydrogen peroxide.

This electrode C2 made of a platinum electrode covered with protein membrane was incorporated into the flow type measuring apparatus shown in FIG. 1, and while passing 100 mM phosphate buffer solution 1 at pH 6.0, a potential of 0.6 V to the Ag/AgCl electrode 8 was applied. In this state, 5 mM hydrogen peroxide was injected from the injector 3, and the detected current was 296 nA. When a solution of 5 mM ascorbic acid was injected, the detected current was 144 nA. Therefore, as shown in Table 1, the rate of the detected current due to ascorbic acid to the detected current due to hydrogen peroxide at the same concentration was 48.5%. The selective permeable membrane obtained by adding 1,4-diaminobutane was inferior in the selective permeability, and it was found that the sample containing ascorbic acid as impeding substance could not be measured in the electrode C2. Besides, the selectivity was further lowered by ultrasonic treatment, and hence it was also known that the physical strength was inferior, too.

Reference 3

Bovine serum albumin (fraction V, made by Sigma Co.) was used as the protein, glutaraldehyde as the crosslinking agent, and tirethylene tetra-amine as the substance reacting with the crosslinking agent other than the protein.

In a Wassermann test tube,

| | |
|---|---|
| 5% bovine serum albumin aqueous solution | 400 μl |
| 25% glutaraldehyde aqueous solution | 20 μl |
| 0.5% triethylene tetra-amine solution | 20 μl |
| distilled water | 560 μl | were mixed, and a mixed solution with the final concentrations of

2% bovine serum albumin
0.5% glutaraldehyde
0.01% triethylene tetra-amine was prepared.

On the other hand, the side surface of a platinum wire of 2 mm in diameter which is an electrically conductive base was coated with a heat-shrink Teflon, and the top of the platinum wire was polished with an emery paper of 1600 count. On the polished surface, 5 μl of the mixed solution was put by using a microsyringe, and dried at 40° C., and a protein membrane was thus directly formed on the platinum electrode. This finished the fabrication of the electrode C3 for detecting hydrogen peroxide.

This electrode C3 made of a platinum electrode covered with protein membrane was incorporated into the flow type measuring apparatus shown in the drawing, and while passing 100 mM phosphate buffer solution 1 at pH 6.0, a potential of 0.6 V to the Ag/AgCl electrode 8 was applied. In this state, 5 mM hydrogen peroxide was injected from the injector 3, and the detected current was 426 nA. When a solution of 5 mM ascorbic acid was injected, the detected current was 104 nA. Therefore, as shown in Table 1, the rate of the detected current due to ascorbic acid to the detected current due to hydrogen peroxide at the same concentration was 24.4%. The selective permeable membrane obtained by adding triethylene tetra-amine was inferior in the selective permeability, and it was found impossible to measure the sample containing ascorbic acid as impeding substance with the electrode C3. When ultrasonically treated, the selectivity was further lowered, and hence it was known that the physical strength was also inferior.

Reference 4

Bovine serum albumin (fraction V, made by Sigma Co.) was used as the protein, glutaraldehyde as the crosslinking agent.

In a Wassermann test tube,

| | |
|---|---|
| 5% bovine serum albumin aqueous solution | 400 μl |
| 25% glutaraldehyde aqueous solution | 20 μl |
| distilled water | 580 μl | were mixed, and a mixed solution with the final concentrations of

2% bovine serum albumin
0.5% glutaraldehyde was prepared

On the other hand, the side surface of a platinum wire of 2 mm in diameter which is an electrically conductive base was coated with a heat-shrink Teflon, and this section was polished with an emery paper of 1600 count. On the polished surface, 5 μl of the mixed solution was put by using a microsyringe, and dried at 40° C., and a protein membrane was thus directly formed on the platinum electrode. This finished the fabrication of the electrode C4 for detecting hydrogen peroxide.

This electrode C4 made of a platinum electrode covered with protein membrane was incorporated into the flow type measuring apparatus shown in the drawing, and while passing 100 mM phosphate buffer solution 1 at pH 6.0, a potential of 0.6 V to the Ag/AgCl electrode 8 was applied. In this state, 5 mM hydrogen peroxide was injected from the injector 3, and the detected current was 219 nA. When a solution of 5 mM ascorbic acid was injected, the detected current was 2.6 nA. Therefore, as shown in Table 1, the rate of the detected current due to ascorbic acid to the detected current due to hydrogen peroxide at the same concentration was 1.2%. Thus, the selective permeable membrane composed of only protein and crosslinking agent was superior in its selective permeability.

This electrode C4 was treated for 10 minutes in an ultrasonic treating apparatus, and was incorporated again into the flow type measuring apparatus shown in FIG. 1. When 5 mM hydrogen peroxide was injected, the detected current was 262 nA, and when 5 mM ascorbic acid solution was injected, the detected current was 6.6 nA.

This result is shown in Table 2, together with the result before ultrasonic treatment. It is known from Table 2 that the sensitivity of the electrode C4 to hydrogen peroxide and ascorbic acid is raised after ultrasonic treatment, and the selective permeability is worsened. Therefore, in such electrode C4, the physical strength is insufficient, and the durability was found to be inferior.

EXAMPLE 4

The side surface of a platinum wire of 2 mm in diameter was covered with heat-shrink Teflon, and the top of the platinum wire is polished with an emery paper of 1600 count, and on this surface a selective permeable membrane was formed in the same materials and same procedure as in Example 1. On this membrane, a mixed solution of 1 mg/ml of bovine serum albumin, 1 mg/ml of glucose oxidase (type II, made by Sigma Co.), and 0.2% of glutaraldehyde dissolved in 100 mM sodium phosphate buffer solution (pH 6.0) was dropped by 3 μl by means of a microsyringe, and by heating for 15 minutes at 40° C., an immobilized enzyme layer was formed, and an electrode E4 was obtained.

This electrode E4 was incorporated into the flow type measuring apparatus shown in FIG. 1, and while passing 100 mM phosphate buffer solution 1 at pH 6.0, a voltage of 0.6 V was applied to the Ag/AgCl electrode 8. When 5 μl of glucose aqueous solution of 30 mM was injected from the injector 3, the detected current was 393 nA. When the same volume of ascorbic acid aqueous solution of 30 mM was injected, the detected current was 11.2 nA. That is, the detected value of ascorbic acid to the glucose of the same concentration was 2.8%, accordingly little effect of the ascorbic acid which could be practically ignored.

This electrode E4 was once dismounted from the flow type measuring apparatus, and was treated for 10 minutes in an ultrasonic treating apparatus, and was put back to the flow type measuring apparatus. Same as before ultrasonic treatment, 5 μl each of 30 mM glucose and ascorbic acid aqueous solution was injected. The detected current to glucose was 395 nA, and the detected current to ascorbic acid was 11.1 nA. This result is shown in Table 3. Thus, this electrode E4 was not changed in performance by ultrasonic treatment.

After the ultrasonically treated electrode was stored in buffer solution at room temperature for 3 months, lowering of sensitivity or selectivity was not recognized, and an excellent durability was shown.

TABLE 3

|  |  | Detected current before ultrasonic treatment (nA) | Detected current after ultrasonic treatment (nA) |
| --- | --- | --- | --- |
| Example 4 | Glucose | 393 | 395 |
|  | Ascorbic acid | 11.2 | 11.1 |
| Reference 5 | Glucose | 385 | 402 |
|  | Ascorbic acid | 10.3 | 16.2 |

Referemce 5

An immobilized enzyme electrode C5 was prepared in the same manner as in Example 4, except that chitosan was not contained when preparing the selective permeable membrane.

This electrode C5 was incorporated into the flow type measuring apparatus shown in FIG. 1, and while passing 100 mM phosphate buffer solution 1 at pH 6.0, a voltage of 0.6 V to the Ag/AgCl electrode was applied. When 5 μl of 30 mM glucose aqueous solution was injected, the detected current was 385 nA. When the same volume of 30 mM ascorbic acid aqueous solution was injected, the detected current was 10.3 nA.

Furthermore, this electrode C5 was once detached from the flow type measuring apparatus, and was treated for 10 minutes in an ultrasonic treating apparatus. Visually there was no abnormality in the membrane, but when the electrode was mounted again on the flow type measuring apparatus, and 5 μl each of 30 mM glucose and ascrobic acid aqueous solution was injected same as before ultrasonic treatment, the detected current to glucose was 402 nA and the detected current to ascorbic acid was 16.2 nA. This result is shown in Table 3, together with the result of Example 4. Thus, in the electrode C5, the membrane permeability was changed by ultrasonic treatment, and the selectivity was lowered.

Besides, the ultrasonically treated electrode was stored in a buffer solution at room temperature for 2 months, peeling was noted in the membrane visually, and it is considered that the partial tear of the membrane induced by ultrasonic treatment was advanced to peeling of the membrane.

As evident from the foregoing examples, according to the invention, when building up a functional membrane possessing a selective permeability by using protein, it is possible to prepare a selective permeable membrane excellent in physical strength easily, without adversely affecting the characteristics of the immobilized protein membrane.

EXAMPLE 5

1. Measuring apparatus

In this example, the flow type measuring apparatus shown in FIG. 1 was used.

2. Preparation of immobilized enzyme electrode E5

Bovine serum albumin (fraction V, made by Sigma Co.) and glucose oxidase (type II, made by Sigma Co.) were used as the protein, glutaraldehyde as the aldehyde, and sodium acetate as the carbonate.

| | |
| --- | --- |
| 5% bovine serum albumin aqueous solution | 100 μl |
| 5% glucose oxidase aqueous solution | 100 μl |
| 1M sodium acetate aqueous solution | 100 μl |
| 10% glutaraldehyde aqueous solution | 100 μl |
| 100 mM phosphate buffer solution (pH 7) | 600 μl | were mixed, and a mixed solution with the final concentrations of 0.5% bovine serum albumin
0.5% glucose oxidase
1.0% glutaraldehyde
100 mM sodium acetate was prepared. The pH of this mixed solution was 7.0.

After letting stand this mixed solution for 20 minutes at room temperature, and 5 μl of the solution was put on the surface of the selective permeable membrane formed on the platinum wire in example 1 by using a microsyringe, dried at 40° C., and an immobilized enzyme electrode E5 was obtained.

3. Measurement

This immobilized glucose oxidase electrode E5 was incorporated into the flow type measuring apparatus shown in FIG. 1, and while passing 100 mM phosphate buffer (pH 6.0) 1, a potential of 0.6 V to Ag/AgCl reference electrode 8 was applied, and 5 mM hydrogen peroxide was injected, and the detected current was 145 nA. When 5 mM glucose solution was injected, the detected current was 36 nA. Therefore, as shown in Table 4, the rate of the detected current due to glucose to the detected current due to hydrogen peroxide at the same concentration was 25%.

TABLE 4

|  | Hydrogen peroxide | Glucose |
| --- | --- | --- |
| Example 5 | 100% | 25% |
| Example 6 | 100% | 25% |

Thus, after preparation of a mixed solution of protein containing carboxylate and glutaraldehyde, if letting stand for 20 minutes at room temperature, the mixed solution could be easily spread on a carrier such as platinum wire, and the immobilized enzyme electrode could be manufactured with a sufficient time allowance.

Besides, as known from Table 4, by the addition of carboxylate, the activity of the enzyme electrode was not affected at all. Furthermore, after storing this electrode E5 in 100 mM phosphate buffer at pH 6.0 for 90 days at room temperature, when it was put back into the same measuring apparatus and the sensitivity to glucose was measured, the same sensitivity was obtained, and it was confirmed that the enzyme was stably immobilized.

EXAMPLE 6

Bovine serum albumin (fraction V, made by Sigma Co.) and glucose oxidase (type II, made by Sigma Co.) were used as the protein, glutaraldehyde was used as aldehyde.

In a Wassermann test tube,

| | |
|---|---|
| 5% bovine serum albumin aqueous solution | 100 μl |
| 5% glucose oxidase solution | 100 μl |
| 10% glutaraldehyde aqueous solution | 100 μl |
| 100 mM phosphate buffer solution (pH 7) | 700 μl | were mixed, and a mixed solution with the final concentrations of 0.5% bovine serum albumin
0.5% glucose oxidase
1.0% glutaraldehyde was prepared.

Right after preparation of this mixed solution, 5 μl was put on the surface of the selective permeable membrane formed on the platinum wire in example 1 by using a microsyringe, dried at 40° C., and an immobilized enzyme electrode E6 was obtained.

This immobilized glucose oxidase electrode was incorporated into a flow type measuring apparatus shown in FIG. 1, and while passing 100 mM phosphate buffer solution, a potential of 0.6 V to Ag/AgCl reference electrode 8 was applied, and when 5 mM hydrogen peroxide was injected, the detected current was 143 nA and when 5 mM glucose solution was injected, the detected current was 36 nA. Thus, as shown in Table 4, the rate of the detected current due to glucose to the detected current due to hydrogen peroxide at the same concentration was 25%. In this example, after preparation of protein-glutaraldehyde mixed solution, the solution was spread promptly on the electrode, and excellent electrode is obtained. But the mixed solution tend to increase in viscosity, which was a limitation for fabrication of electrode.

As evident from the description of the embodiments herein, according to the invention, when immobilizing enzyme by using polyhydric aldehyde, it is easily possible to immobilize the homogeneous and quantitative immobilized enzyme membrane continuously and at high reproducibility, without adversely affecting the enzyme.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. An electrode comprising:
   an electrically conductive base, and
   a selectively permeable membrane having an inner surface and an outer surface, said inner surface being disposed on or near said electrically conductive base, and said membrane being comprised of a crosslinked reaction product of a solution comprising (a) albumin, (b) a crosslinking agent capable of covalently bonding with an amino group or derivative thereof, and (c) chitosan, wherein said albumin is immobilized in said selectively permeable membrane by the crosslinking reaction, wherein said selectively permeable membrane is selectively permeable to an electrochemically detectable substance while being impermeable to higher molecular weight materials, and wherein the substance must pass through said selectively permeable membrane to contact said electrically conductive base.

2. The electrode according to claim 1, wherein said crosslinking agent is glutaraldehyde or hexamethylene di-isocyanate.

3. The electrode according to claim 1, wherein the composition ratio by weight of albumin to chitosan is in a range of 1000:1 to 1000:10.

4. The electrode according to claim 1, wherein the composition ratio by weight of albumin to said crosslinking agent is in a range of 100.5 to 100:50.

5. The electrode according to claim 1, further comprising an immobilized enzyme membrane disposed on or near said outer surface of said selectively permeable membrane and comprised of an enzyme, wherein said enzyme is capable of producing the electrochemically detectable substance which can permeate said selectively permeable membrane.

6. The electrode according to claim 5, wherein said enzyme is an oxidase enzyme.

7. An electrode according to claim 5 or 6, wherein the immobilized enzyme membrane is a crosslinked reaction product of a solution comprising a carboxylate, said enzyme and an aldehyde as a crosslinking agent, and wherein the crosslinking reaction is promoted by heating or drying, thereby immobilizing the enzyme.

8. The electrode according to claim 7, wherein the pH of the mixed solution of enzyme and aldehyde containing the carboxylate is in a range of 5 to 8.

9. The electrode according to claim 7, wherein the molecular weight of the carboxylic acid of the carboxylate is 46 to 300.

* * * * *